United States Patent
Almogy et al.

(10) Patent No.: US 12,152,277 B2
(45) Date of Patent: Nov. 26, 2024

(54) METHODS FOR PROCESSING PAIRED END SEQUENCES

(71) Applicant: ULTIMA GENOMICS, INC., Newark, CA (US)

(72) Inventors: Gilad Almogy, Palo Alto, CA (US); Mark Pratt, Bozeman, MT (US); Florian Oberstrass, Menlo Park, CA (US)

(73) Assignee: Ultima Genomics, Inc., Fremont, CA (US)

( * ) Notice: Subject to any disclaimer, the term of this patent is extended or adjusted under 35 U.S.C. 154(b) by 0 days.

(21) Appl. No.: 18/132,693

(22) Filed: Apr. 10, 2023

(65) Prior Publication Data

US 2023/0348965 A1    Nov. 2, 2023

Related U.S. Application Data (63) Continuation of application No. 16/842,584, filed on Apr. 7, 2020, now Pat. No. 11,655,501, which is a continuation of application No. PCT/US2018/056593, filed on Oct. 18, 2018.

(60) Provisional application No. 62/574,629, filed on Oct. 19, 2017.

(51) Int. Cl.
*C12Q 1/68*    (2018.01)
*C12Q 1/6806*  (2018.01)
*C12Q 1/6869*  (2018.01)

(52) U.S. Cl.
CPC ......... *C12Q 1/6869* (2013.01); *C12Q 1/6806* (2013.01)

(58) Field of Classification Search
CPC ............................ C12Q 1/6869; C12Q 1/6806
See application file for complete search history.

(56) References Cited

U.S. PATENT DOCUMENTS

| | | | |
|---|---|---|---|
| 11,655,501 B2 * | 5/2023 | Almogy | C12Q 1/6806 |
| | | | 435/6.12 |
| 2008/0199872 A1 | 8/2008 | Barnard et al. | |
| 2014/0335528 A1 | 11/2014 | Olejnik et al. | |
| 2015/0361481 A1 * | 12/2015 | Joun | C12Q 1/6846 |
| | | | 506/26 |
| 2016/0019341 A1 | 1/2016 | Harris et al. | |

FOREIGN PATENT DOCUMENTS

| | | |
|---|---|---|
| WO | WO-2014210353 A2 | 12/2014 |
| WO | WO-2017161306 A1 | 9/2017 |
| WO | WO-2017176896 A1 | 10/2017 |
| WO | WO-2019079653 A1 | 4/2019 |

OTHER PUBLICATIONS

Holmberg et al., The biotin-streptavidin interaction can be reversibly broken using water at elevated temperatures. Electrophoresis, vol. 26, No. 3, pp. 501-510 (2005).
PCT/US2018/056593 International Search Report & Written Opinion dated Jan. 3, 2019.

* cited by examiner

*Primary Examiner* — Jezia Riley
(74) *Attorney, Agent, or Firm* — Schmidt Patent Law, Inc.

(57) ABSTRACT

Recognized herein is the need for methods and processes for increasing the efficiency and accuracy of paired end sequencing.

20 Claims, 6 Drawing Sheets

METHODS FOR PROCESSING PAIRED END SEQUENCES

CROSS-REFERENCE

This application is a continuation of U.S. patent application Ser. No. 16/842,584, filed Apr. 7, 2020, which is a continuation of International Patent Application No. PCT/US2018/056593, filed Oct. 18, 2018, which claims the benefit of U.S. Provisional Patent Application No. 62/574,629, filed Oct. 19, 2017, each of which applications is entirely incorporated herein by reference.

BACKGROUND

Advances in the study of biological molecules have been led, in part, by improvements in technologies used to characterize molecules or their biological reactions. In particular, the study of nucleic acids has benefited from developing technologies used for sequence analysis. Sequencing of nucleic acids has various applications in the fields of molecular biology and medicine (e.g., diagnosis). Nucleic acid sequencing may provide information that may be used to diagnose a certain condition in a subject and in some cases tailor a treatment plan. Sequencing is widely used for molecular biology applications, including vector designs, gene therapy, vaccine design, industrial strain design and verification. The preparation of samples for use in eventual sequence analysis may play a role in the type and quality of information that may be obtained in such analysis.

SUMMARY

The technique of paired end may allow the determination of two "reads" of sequence from two locations on a single polynucleotide duplex. The advantage of the paired end approach is that there is significantly more information to be gained from sequencing two stretches each of N (N>1) bases from a single template then from sequencing N bases from each of two independent templates in a random fashion. Recognized herein is the need for methods and processes for increasing the efficiency and accuracy of paired end sequencing.

An aspect of the present disclosure provides a method for processing a biological sample. The method comprises: (a) providing a first set of beads and a second set of beads, wherein a first bead of the first set of beads comprises a first primer having sequence complementarity with a first adaptor coupled to a first strand of the biological sample, wherein a second bead of the second set of beads comprises a second primer having sequence complementarity with a second adaptor coupled to a second strand of the biological sample, and wherein the first primer is different than the second primer; (b) partitioning (i) the first bead of the first set of beads, (ii) the second bead of the second set of beads, and (iii) the biological sample comprising the first adaptor coupled to the first strand and the second adaptor coupled to the second strand, in a partition of a plurality of partitions; and (c) subjecting the partition to conditions sufficient to amplify the first strand and the second strand to generate one or more copies of the first strand coupled to the first bead and one or more copies of the second strand coupled to the second bead, wherein the one or more copies of the first strand at least partially overlap the one or more copies of the second strand.

In some embodiments, the first bead of the first set of beads is releasably coupled to the second bead of the second set of beads in a releasably coupled bead pair. In some embodiments, the first bead and the second bead of the releasably coupled bead pair is coupled through protein interactions or covalent bonds. In some embodiments, the method further comprises subjecting the first bead releasably coupled to the second bead to a stimulus, thereby releasing the first bead from the second bead. In some embodiments, the stimulus is a temperature change.

In some embodiments, the first bead of the first set of beads is irremovably coupled to the second bead of the second set of beads. In some embodiments, the first bead is coupled to the second bead through cross-linking.

In some embodiments, the method further comprises, prior to (a), synthesizing the first set of beads or the second set of beads.

In some embodiments, the method further comprises, prior to (a), synthesizing the first set of beads and the second set of beads. In some embodiments, synthesizing the first set of beads and the second set of beads results in a set of releasably coupled bead pairs each comprising a first bead of the first set of beads and a second bead of the second set of beads. In some embodiments, the method further comprises, subsequent to synthesizing the set of releasably coupled bead pairs, performing size selection, thereby discriminating between the releasably coupled bead pairs and other combinations of first beads and/or second beads. In some embodiments, synthesizing the first set of beads and the second set of beads generates a set of irremovably coupled bead pairs each comprising a first bead of the first set of beads and a second bead of the second set of beads. In some embodiments, the method further comprises subsequent to synthesizing the set of irremovably coupled bead pairs, performing size selection, thereby discriminating between the irremovably coupled bead pairs and other combinations of first beads and/or second beads.

In some embodiments, the method further comprises subsequent to (c), subjecting the one or more copies of the first strand and the one or more copies of the second strand to nucleic acid sequencing. In some embodiments, the nucleic acid sequencing comprises sequencing by synthesis. In some embodiments, the nucleic acid sequencing comprises polymerase chain reaction (PCR). In some embodiments, the nucleic acid sequencing comprises emulsion polymerase chain reaction (emPCR).

In some embodiments, the first adaptor comprises a first sub-part and a second sub-part, wherein the first sub-part has sequence complementarity to the second sub-part.

In some embodiments, the second adaptor comprises a first sub-part and a second sub-part, wherein the first sub-part has sequence complementarity to the second sub-part.

In some embodiments, each the partition of the plurality of partitions comprises (i) at least one of the first bead of the first set of beads, (ii) at least one of the second bead of the second set of beads, and (iii) the biological sample comprising the first adaptor coupled to the first strand and the second adaptor coupled to the second strand.

In another aspect, the present disclosure provides a method for processing a biological sample comprising: (a) providing a first set of beads and a second set of beads, wherein a first bead of the first set of beads comprises a first primer having sequence complementarity with a first adaptor coupled to a first strand of the biological sample, wherein a second bead of the second set of beads comprises a second primer having sequence complementarity with a second adaptor coupled to a second strand of the biological sample, and wherein the first primer is different than the second primer; (b) partitioning (i) the first bead of the first set of beads, (ii) the second bead of the second set of beads, and (iii) the biological sample comprising the first adaptor coupled to the first strand and the second adaptor coupled to the second strand, in a partition of a plurality of partitions; and (c) subjecting the partition to conditions sufficient to amplify the first strand and the second strand to generate one or more copies of the first strand coupled to the first bead and one or more copies of the second strand coupled to the second bead, wherein the one or more copies of the first strand have at most partial overlap with the one or more copies of the second strand.

In some embodiments, the one or more copies of the first strand have no overlap with the one or more copies of the second strand.

In some embodiments, (a) further comprises providing a synthetic nucleic acid molecule. In some embodiments, the synthetic nucleic acid molecule is a double-stranded nucleic acid molecule. In some embodiments, (b) comprises partitioning the synthetic nucleic acid molecule in the partition. In some embodiments, the synthetic nucleic acid molecule comprises a cleavable element. In some embodiments, the cleavable element allows separation of a component of the synthetic nucleic acid molecule. In some embodiments, the cleavable element allows separation of the synthetic nucleic acid molecule by chemical, light, heat, or other mechanisms.

In some embodiments, the method further comprises, subsequent to (c), subjecting the synthetic nucleic acid molecule to ligation and circularization. In some embodiments, the method further comprises subsequent to the ligation and circularization, subjecting the synthetic nucleic acid molecule to cleaving, thereby generating a cleaved synthetic nucleic acid molecule. In some embodiments, the method further comprises subjecting the cleaved synthetic nucleic acid molecule to gap filling through a nucleic acid amplification reaction.

In some embodiments, the first bead of the first set of beads is releasably coupled to the second bead of the second set of beads in a releasably coupled bead pair. In some embodiments, the first and second beads of the releasably coupled bead pair are releasably coupled through protein interactions or covalent bonds. In some embodiments, the method further comprises subjecting the releasably coupled bead pair to a stimulus, thereby releasing the first bead from the second bead. In some embodiments, the stimulus is a temperature change.

In some embodiments, the first bead of the first set of beads is irremovably coupled to the second bead of the second set of beads in an irremovably coupled bead pair.

In some embodiments, the first bead is coupled to the second bead through cross-linking.

In some embodiments, the method further comprises, prior to (a), synthesizing the first set of beads or the set of second beads.

In some embodiments, the method further comprises, prior to (a), synthesizing the first set of beads and the set of second beads. In some embodiments, synthesizing the first set of beads and the second set of beads results in a set of releasably coupled bead pairs each comprising a first bead of the first set of beads and a second bead of the second set of beads. In some embodiments, the method further comprises subsequent to synthesizing the set of releasably coupled bead pairs, performing size selection, thereby discriminating between the releasably coupled bead pairs and other combinations of first beads and/or second beads. In some embodiments, synthesizing the first set of beads and the second set of beads generates a set of irremovably coupled bead pairs each comprising a first bead of the first set of beads and a second bead of the second set of beads. In some embodiments, the method further comprises subsequent to synthesizing the set of irremovably coupled bead pairs, performing size selection, thereby discriminating between the irremovably coupled bead pairs and other combinations of first beads and/or second beads.

In some embodiments, the method further comprises subsequent to (c), subjecting the one or more copies of the first strand and the one or more copies of the second strand to nucleic acid sequencing. In some embodiments, the nucleic acid sequencing comprises sequencing by synthesis. In some embodiments, the nucleic acid sequencing comprises polymerase chain reaction (PCR). In some embodiments, the nucleic acid sequencing comprises emulsion polymerase chain reaction (emPCR).

In some embodiments, the first adaptor comprises a first sub-part and a second sub-part, wherein the first sub-part has sequence complementarity to the second sub-part.

In some embodiments, the second adaptor comprises a first sub-part and a second sub-part, wherein the first sub-part has sequence complementarity to the second sub-part.

In some embodiments, each the partition of the plurality of partitions comprises (i) at least one of the first bead of the first set of beads, (ii) at least one of the second bead of the second set of beads and (iii) the biological sample comprising the first adaptor coupled to the first strand and the second adaptor coupled to the second strand.

Another aspect of the present disclosure provides a non-transitory computer-readable medium comprising machine-executable code that, upon execution by one or more computer processors, implements any of the methods disclosed above or elsewhere herein.

Another aspect of the present disclosure provides a system comprising one or more computer processors and memory coupled thereto. The memory may comprise a non-transitory computer-readable medium comprising machine-executable code that, upon execution by the one or more computer processors, implements any of the methods disclosed above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "sequencing," as used herein, generally refers to a process for generating or identifying a sequence of a biological molecule, such as a nucleic acid molecule. Such sequence may be a nucleic acid sequence, which may include a sequence of nucleic acid bases. Sequencing may be single molecule sequencing or sequencing by synthesis, for example. Sequencing may be performed using template nucleic acid molecules immobilized on a support, such as a flow cell or one or more beads.

The term "read," as used herein, generally refers to a nucleic acid sequence, such as a sequencing read. Such sequencing read may be generated by a nucleic acid sequencer, such as a massively parallel array sequencer (e.g., Illumina or Pacific Biosciences of California). A sequencing read may include a portion, at least portion or all of a genome of a subject. The sequencing read may be part of a collection of sequencing reads, which may be combined through, for example, alignment, to yield a sequence of a genome of the subject.

The term "subject," as used herein, generally refers to an individual having a biological sample that is undergoing processing or analysis. A subject can be an animal or plant. The subject can be a mammal, such as a human, dog, cat, horse, pig or rodent. The subject can have or be suspected of having a disease, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. The subject can have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, velocardiofacial syndrome, WAGR syndrome, or Wilson disease.

As used herein, the term "biological sample" generally refers to a sample obtained from a subject. In some cases, the biological sample is obtained directly from the subject. A biological sample obtained directly from a subject may not have been further processed after being obtained from the subject. For example, blood is obtained directly from a subject by accessing the subject's circulatory system, removing the blood from the subject (e.g., via a needle), and entering the removed blood into a receptacle. The receptacle may comprise reagents (e.g., anti-coagulants) such that the blood sample is useful for further analysis. In another example, a swab may be used to access epithelial cells on an oropharyngeal surface of the subject. After obtaining the biological sample from the subject, the swab containing the biological sample can be contacted with a fluid (e.g., a buffer) to collect the biological fluid from the swab.

In some cases, a biological sample (e.g., a biological sample comprising one or more nucleic acid molecules) may not be purified when provided in a reaction vessel. In other cases, for a biological sample comprising one or more nucleic acid molecules, the one or more nucleic acid molecules may not be extracted when the biological sample is provided to a reaction vessel. For example, ribonucleic acid (RNA) and/or deoxyribonucleic acid (DNA) of a biological sample may not be extracted from the biological sample when providing the biological sample to a reaction vessel. Moreover, in some cases, a target nucleic acid (e.g., a target RNA or target DNA) present in a biological sample may not be concentrated prior to providing the biological sample to a reaction vessel.

Any suitable biological sample that comprises one or more nucleic acid molecules may be obtained from a subject. A biological sample may be solid matter (e.g., biological tissue) or may be a fluid (e.g., a biological fluid). In general, a biological fluid can include any fluid associated with living organisms. Non-limiting examples of a biological sample include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, microbiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues.

The biological sample may be a solid tissue or fluid sample. In some examples, the biological sample is a cell-free (or cell free) sample. Such sample may include cell-free nucleic acid molecules, such as cell-free DNA and/or RNA.

A biological sample may be obtained from a subject by any approach. Non-limiting examples of approaches to obtain a biological sample directly from a subject include accessing the circulatory system (e.g., intravenously or intra-arterially via a syringe or other needle), collecting a secreted biological sample (e.g., feces, urine, sputum, saliva, etc.), surgically (e.g., biopsy), swabbing (e.g., buccal swab, oropharyngeal swab), pipetting, and breathing. Moreover, a biological sample may be obtained from any anatomical part of a subject where a desired biological sample is located.

In any various aspects, a biological sample may contain a target nucleic acid. As used herein, the terms "template nucleic acid", "target nucleic acid", "nucleic acid molecule," "nucleic acid sequence," "nucleic acid fragment," "oligonucleotide," "polynucleotide," and "nucleic acid" generally refer to polymeric forms of nucleotides of any length, such as deoxyribonucleotides (dNTPs) or ribonucleotides (rNTPs), or analogs thereof. Nucleic acids may have any three dimensional structure, and may perform any function, known or unknown. A nucleic acid molecule can have a length of at least about 10 nucleic acid bases ("bases"), 20 bases, 30 bases, 40 bases, 50 bases, 100 bases, 200 bases, 300 bases, 400 bases, 500 bases, 1 kilobase (kb), 2 kb, 3 kb, 4 kb, 5 kb, 10 kb, 50 kb, or more. An oligonucleotide is typically composed of a specific sequence of four nucleotide bases: adenine (A); cytosine (C); guanine (G); and thymine (T) (uracil (U) for thymine (T) when the polynucleotide is RNA). Oligonucleotides may include one or more nonstandard nucleotide(s), nucleotide analog(s) and/or modified nucleotides. Non-limiting examples of nucleic acids include DNA, RNA, genomic DNA, synthetic DNA/RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, complementary DNA (cDNA), recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation or binding with a reporter agent.

In any of the various aspects, a target nucleic acid may be amplified to generate an amplified product. A target nucleic acid may be a target RNA or a target DNA. In cases where the target nucleic acid is a target RNA, the target RNA may be any type of RNA, including types of RNA described elsewhere herein. In some cases, the target RNA is viral RNA. In some cases, the viral RNA may be pathogenic to the subject. Non-limiting examples of pathogenic viral RNA include human immunodeficiency virus I (HIV I), human immunodeficiency virus n (HIV 11), orthomyxoviruses, Ebola virus, Dengue virus, influenza viruses (e.g., H1N1, H3N2, H7N9, or H5N1), herpesvirus, hepatitis A virus, hepatitis B virus, hepatitis C (e.g., armored RNA-HCV virus) virus, hepatitis D virus, hepatitis E virus, hepatitis G virus, Epstein-Barr virus, mononucleosis virus, cytomegalovirus, SARS virus, West Nile Fever virus, polio virus, and measles virus.

In any of the various aspects of the present disclosure, the methods described herein may be conducted in a reaction vessel (e.g., a droplet in an emulsion, or a well among a plurality of wells). Any suitable reaction vessel may be used. In some examples, a reaction vessel comprises a body that can include an interior surface, an exterior surface, an open end, and an opposing closed end. In some cases, a reaction vessel may comprise a cap. The cap may be configured to contact the body at its open end, such that when contact is made the open end of the reaction vessel is closed. In some cases, the cap is permanently associated with the reaction vessel such that it remains attached to the reaction vessel in open and closed configurations. In some cases, the cap is removable, such that when the reaction vessel is open, the cap is separated from the reaction vessel. In some examples, a reaction vessel may be sealed, optionally hermetically sealed.

A reaction vessel may be of varied size, shape, weight, and configuration. Some reaction vessels may be round or oval tubular shaped. Some reaction vessels may be rectangular, square, diamond, circular, elliptical, or triangular shaped. A reaction vessel may be regularly shaped or irregularly shaped. The closed end of a reaction vessel may have a tapered, rounded, or flat surface. Non-limiting examples of types of a reaction vessel include a tube, a well, a capillary tube, a cartridge, a cuvette, a centrifuge tube, or a pipette tip. Reaction vessels may be constructed of any suitable material with non-limiting examples of such materials that include glasses, metals, plastics, and combinations thereof.

In some cases, a reaction vessel is part of an array of reaction vessels. An array of reaction vessels may be particularly useful for automating methods and/or simultaneously processing multiple samples. For example, a reaction vessel may be a well of a microwell plate comprised of a number of wells. In another example, a reaction vessel may be held in a well of a thermal block of a thermocycler, wherein the block of the thermal cycle comprises multiple wells each capable of receiving a sample vessel. An array comprised of reaction vessels may comprise any appropriate number of reaction vessels. An array may include at least 1, 2, 3, 4, 5, 6, 7, 8, 9, 10, 20, 30, 40, 50, 100, 200, 300, 400, 500, 1000, 10000 or more vessels. For example, an array may comprise at least 2, 4, 6, 8, 10, 12, 14, 16, 18, 20, 25, 35, 48, 96, 144, 384, or more reaction vessels. A reaction vessel part of an array of reaction vessels may also be individually addressable by a fluid handling device, such that the fluid handling device can correctly identify a reaction vessel and dispense appropriate fluid materials into the reaction vessel. Fluid handling devices may be useful in automating the addition of fluid materials to reaction vessels.

In some cases, a reaction vessel may comprise multiple thermal zones. Thermal zones within a reaction vessel may be achieved by exposing different regions of the reaction vessel to different temperature cycling conditions. For example, a reaction vessel may comprise an upper thermal zone and a lower thermal zone. The upper thermal zone may be capable of a receiving a biological sample and reagents necessary to obtain a reaction mixture for nucleic acid amplification. The reaction mixture can then be subjected to a first thermocycling protocol. After a desired number of cycles, for example, the reaction mixture can slowly, but continuously leak from the upper thermal zone to the lower thermal zone. In the lower thermal zone, the reaction mixture is then subjected to a desired number of cycles of a second thermocycling protocol different from that in the upper thermal zone. Such a strategy may be particularly useful when nested PCR is used to amplify DNA. In some embodiments, thermal zones may be created within a reaction vessel with the aid of thermal sensitive layering materials within the reaction vessels. In such cases, heating of the thermal sensitive layering materials may be used to release reaction mixtures from one thermal zone to the next. In some embodiments, the reaction vessel comprises 2, 3, 4, 5, 6, 7, 8, 9, 10, 11, 12, 13, 14, 15, 20 or more thermal zones.

The term "bead" includes a solid support, resin, hydrogel, colloid or particle of any shape and dimensions. The bead may comprise any suitable material such as glass or ceramic, one or more polymers and/or metals. Examples of suitable polymers may be nylon, polytetrafluoroethylene, polystyrene, polyacrylamide, agarose, cellulose, cellulose derivatives, or dextran. Examples of suitable metals include paramagnetic metals, such as iron. The bead may be magnetic or non-magnetic. The bead may have one or more different dimensions including a diameter. A dimension of the bead (e.g., the diameter of the bead) may be less than about 1 mm, less than about 0.1 mm, less than about 0.01 mm, less than about 0.005 mm, from about 1 nm to about 100 nm, from about 1 μm to about 100 μm, or from about 1 mm to about 100 mm. A collection of beads may comprise one or more beads having the same or different characteristics. For example, a first bead of a collection of beads may have a first diameter and a second bead of the collection of beads may have a second diameter. The first diameter may be the same or approximately the same as or different from the second diameter. Similarly, the first bead may have the same or a different shape and composition than a second bead. In some cases, the first bead may comprise a first material, such as a first oligonucleotide or primer coupled thereto, and a second bead may comprise a second material, such as a second oligonucleotide or primer coupled thereto. The first and second oligonucleotides or primers may be the same or different.

As used herein, the term "primer,"$_{[MY1]}$ generally refers to a strand of nucleic acid that serves as a starting point for nucleic acid synthesis, such as a primer extension reaction which may be a component of a nucleic acid amplification reaction. In general, a primer hybridizes to a template strand and nucleotides may be added to the end(s) of a primer, sometimes with the aid of a polymerizing enzyme such as a polymerase. In an example, during replication of a DNA sample, an enzyme that catalyzes replication starts replication at the 3'-end of a primer attached to the DNA sample and copies the opposite strand. A primer can have one or more functional groups that can be used to couple the primer to a support or carrier, such as a bead or particle.

A primer may be completely or partially complementary to a template nucleic acid. The complementarity or homology or sequence identity between the primer and the template nucleic acid may be limited. The length of the primer may be between 8 nucleotide bases to 50 nucleotide bases. In some cases, the length of the primer may be more than 2 nucleotide bases, more than 3 nucleotide bases, 4 nucleotide bases, 5 nucleotide bases, 6 nucleotide bases, 7 nucleotide bases, 8 nucleotide bases, 9 nucleotide bases, 10 nucleotide bases, 11 nucleotide bases, 12 nucleotide bases, 13 nucleotide bases, 14 nucleotide bases, 15 nucleotide bases, 16 nucleotide bases, 17 nucleotide bases, 18 nucleotide bases, 19 nucleotide bases, 20 nucleotide bases, 21 nucleotide bases, 22 nucleotide bases, 23 nucleotide bases, 24 nucleotide bases, 25 nucleotide bases, 26 nucleotide bases, 27 nucleotide bases, 28 nucleotide bases, 29 nucleotide bases, 30 nucleotide bases, 31 nucleotide bases, 32 nucleotide bases, 33 nucleotide bases, 34 nucleotide bases, 35 nucleotide bases, 37 nucleotide bases, 40 nucleotide bases, 42 nucleotide bases, 45 nucleotide bases, 47 nucleotide bases or 50 nucleotide bases. In some cases, the length of the primer may be less than 50 nucleotide bases, 47 nucleotide bases, 45 nucleotide bases, 42 nucleotide bases, 40 nucleotide bases, 37 nucleotide bases, 35 nucleotide bases, 34 nucleotide bases, 33 nucleotide bases, 32 nucleotide bases, 31 nucleotide bases, 30 nucleotide bases, 29 nucleotide bases, 28 nucleotide bases, 27 nucleotide bases, 26 nucleotide bases, 25 nucleotide bases, 24 nucleotide bases, 23 nucleotide bases, 22 nucleotide bases, 21 nucleotide bases, 20 nucleotide bases, 19 nucleotide bases, 18 nucleotide bases, 17 nucleotide bases, 16 nucleotide bases, 15 nucleotide bases, 14 nucleotide bases, 13 nucleotide bases, 12 nucleotide bases, 11 nucleotide bases, 10 nucleotide bases, 9 nucleotide bases, 8 nucleotide bases, 7 nucleotide bases, 6 nucleotide bases, 5 nucleotide bases, 4 nucleotide bases, 3 nucleotide bases or 2 nucleotide bases.

A primer may exhibit sequence identity or homology or complementarity to the template nucleic acid. The homology or sequence identity or complementarity between the primer and a template nucleic acid may be based on the length of the primer. For example, if the primer length is about 20 nucleic acids, it may contain 10 or more contiguous nucleic acid bases complementary to the template nucleic acid.

As used herein, the term "primer extension reaction" generally refers to the, binding of a primer to a strand of the template nucleic acid, followed by elongation of the primer(s). It may also include, denaturing of a double-stranded nucleic acid and the binding of a primer strand to either one or both of the denatured template nucleic acid strands, followed by elongation of the primer(s). Primer extension reactions may be used to incorporate nucleotides or nucleotide analogs to a primer in template-directed fashion by using enzymes (polymerizing enzymes).

As used herein the term "nucleotide analogs" may include, but are not limited to diaminopurine, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, ethynyl nucleotide bases, 1-propynyl nucleotide bases, azido nucleotide bases, phosphoroselenoate nucleic acids and the like. In some cases, nucleotides may include modifications in their phosphate moieties, including modifications to a triphosphate moiety. Additional, non-limiting examples of modifications include phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates) or modifications with selenium moieties (e.g., phosphoroselenoate nucleic acids). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Nucleotide analogs may be capable of reacting or bonding with detectable moieties for nucleotide detection.

The term "adaptor" as used herein, generally refers to a molecule (e.g., polynucleotide) that is adapted to permit a sequencing instrument to sequence a target polynucleotide, such as by interacting with the target polynucleotide to enable sequencing. The sequencing adaptor permits the target polynucleotide to be sequenced by the sequencing instrument. In an example, the sequencing adaptor comprises a nucleotide sequence that hybridizes or binds to a capture polynucleotide attached to a solid support of a sequencing system, such as a flow cell. In another example, the sequencing adaptor comprises a nucleotide sequence that hybridizes or binds to a polynucleotide to generate a hairpin loop, which permits the target polynucleotide to be sequenced by a sequencing system. The sequencing adaptor can include a sequencer motif, which can be a nucleotide sequence that is complementary to a flow cell sequence of other molecule (e.g., polynucleotide) and usable by the sequencing system to sequence the target polynucleotide. The sequencer motif can also include a primer sequence for use in sequencing, such as sequencing by synthesis. The sequencer motif can include the sequence(s) needed to couple a library adaptor to a sequencing system and sequence the target polynucleotide.

As described herein, the adaptor may have a first sub-part and a second sub-part. The first sub-part and the second sub-part may have sequence complementarity.

The terms "polymerase," "polymerizing enzyme, or "polymerization enzyme," as used herein, generally refer to any enzyme capable of catalyzing a polymerization reaction. A polymerizing enzyme may be used to extend primers with the incorporation of nucleotides or nucleotide analogs. Examples of polymerases include, without limitation, a nucleic acid polymerase. The polymerase can be naturally occurring or synthesized. An example polymerase is a Φ29 polymerase or derivative thereof. A polymerase can be a polymerization enzyme. In some cases, a transcriptase or a ligase is used (i.e., enzymes which catalyze the formation of a bond). Examples of polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. In some embodiments, the polymerase is a single subunit polymerase. The polymerase can have high processivity, namely the capability of the polymerase to consecutively incorporate nucleotides in a nucleic acid template without releasing the nucleic acid template.

The term "at least partially" as used herein, generally refers to any fraction of a whole amount. For example, "at least partially" can refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 99.9% of a whole amount.

The term "barcode" as used herein, generally refers to one or more nucleotide sequences that can be used to identify one or more particular nucleic acids. A barcode can comprise about 1, about 2, about 3, about 4, about 5, about 6, about 7, about 8, about 9, about 10, about 11, about 12, about 13, about 14, about 15, about 16, about 17, about 18, about 19, about 20 or more consecutive nucleotides. In some embodiments, a barcode comprises at least about 10, about 20, about 30, about 40, about 50, about 60, about 70, about 80, about 90, about 100 or more consecutive nucleotides. In some embodiments, all of the barcodes are different. The diversity of different barcodes in a population of nucleic acids comprising barcodes can be randomly generated or non-randomly generated.

Methods

An aspect of the present disclosure provides a method for processing a biological sample. The method may comprise providing a first set of particles (e.g., beads) and a second set of particles (e.g., beads). A first bead of the first set of beads may comprise a first primer having at least partial sequence complementarity with a first adaptor coupled to a first nucleic acid strand of the biological sample (e.g., one or more nucleic acid molecules, such as one or more DNA or RNA molecules). A second bead of the second set of beads may comprise a second primer having sequence complementarity with a second adaptor coupled to a second nucleic acid strand of the biological sample. The first primer may be different from the second primer.

The method may comprise partitioning (e.g., co-partitioning) (i) the first bead of the first set of beads, (ii) the second bead of the second set of beads, and (iii) the biological sample comprising the first adaptor coupled to the first strand and the second adaptor coupled to the second strand, in a partition. The partitioning may be achieved using, for example, one or more droplets (e.g., in an emulsion) or wells.

The partition comprising the first and second beads and the biological sample may be subjected to conditions sufficient to generate one or more copies of the first strand coupled to the first adapter, or complements thereof, and/or one or more copies of the second strand coupled to the second adapter, or complements thereof. Generating the one or more copies of the first strand and/or the second strand, or complements thereof, may involve subjecting the first and second beads and the biological sample to conditions sufficient to perform a primer extension reaction and/or nucleic acid amplification reaction. The first primer of the first bead may be used to generate the one or more copies of the first strand, and/or complements thereof. The one or more copies of the first strand, and/or complements thereof, may be coupled to the first bead. The second primer of the second bead may be used to generate the one or more copies of the second strand, and/or complements thereof. The one or more copies of the second strand, and/or complements thereof, may be coupled to the second bead. The sequences of the one or more copies of the first strand, or complements thereof, may at least partially overlap the sequences of the one or more copies of the second strand, or complements thereof.

Any useful type of reaction (e.g., any nucleic acid amplification reaction) may be used to process a target nucleic acid molecule to generate one or more copies or complements thereof of the target nucleic acid molecule (e.g., an amplified product). In some cases, a single primer extension reaction may be used. In some cases, nucleic acid amplification may be used. Amplification of a nucleic acid may be linear, exponential, or a combination thereof. Amplification may be emulsion based or may be non-emulsion based. Non-limiting examples of nucleic acid amplification methods include reverse transcription, primer extension, polymerase chain reaction, ligase chain reaction, helicase-dependent amplification, asymmetric amplification, rolling circle amplification, and multiple displacement amplification (MDA). In some embodiments, the amplified product may be DNA. In cases where a target RNA is amplified, DNA (e.g., complementary DNA (cDNA)) can be obtained by reverse transcription of the RNA and subsequent amplification of the DNA can be used to generate an amplified DNA product. The amplified DNA product may be indicative of the presence of the target RNA in the biological sample. In cases where DNA is amplified, any DNA amplification method may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). In some cases, DNA amplification is linear. In some cases, DNA amplification is exponential. In some cases, DNA amplification is achieved with nested PCR, which can improve sensitivity of detecting amplified DNA products.

The time period over which amplification yields a detectable amount of amplified product indicative of the presence of a target nucleic acid amplified can vary depending upon the biological sample from which the target nucleic acid was obtained, the particular nucleic acid amplification reactions to be conducted, and the particular number of cycles of amplification reaction desired. For example, amplification of a target nucleic acid may yield a detectable amount of amplified product indicative to the presence of the target nucleic acid over a time period of 120 minutes or less; 90 minutes or less; 60 minutes or less; 50 minutes or less; 45 minutes or less; 40 minutes or less; 35 minutes or less; 30 minutes or less; 25 minutes or less; 20 minutes or less; 15 minutes or less; 10 minutes or less; or 5 minutes or less.

In the method for processing a biological sample, the first bead from the first set of beads may be releasably coupled to the second bead from the second set of beads. Similarly, additional beads of the first set of beads may be releasably coupled to additional beads of the second set of beads, such that there may be a set of releasably coupled first beads and second beads. Releasably coupled first beads and second beads may be coupled through protein interactions or covalent bonds. The protein interactions may be hydrogen bonding or Van der Waal's forces. The covalent bonds may be formed (e.g., synthetically formed) between the beads.

The first bead releasably coupled to the second bead may be subjected to a stimulus that stimulates the release of the first bead from the second bead. The stimulus may comprise a temperature change and/or a chemical stimulus. The first bead of the first set of beads may also be irremovably coupled to the second bead of the second set of beads. This irremovable coupling may comprise cross-linking between the first bead and the second bead.

Prior to the method provided herein for processing a biological sample, the first set of beads or the second set of beads may be prepared. The first set of beads or the second set of beads may be for example, polymer beads. The first and/or second set of beads may have a coating such as a PEG layer or hydrogel. The first and second set of beads may contain the same core bead or different core beads (e.g., comprise the same or different material). For example, the beads of the first set of beads may be prepared from a first material and the beads of the second set of beads may be prepared from a second material, where the first material may be the same as or different from the second material. The first and second primers may be provided to the first set of beads and the second set of beads, respectively, during the preparation (e.g., synthesis) of the first and second sets of beads. Alternatively, the first and second primers may be provided to the first set of beads and the second set of beads, respectively, after preparation of the first and second sets of beads (e.g., to "core beads" that do not yet comprise primers). Where primers are immobilized to beads in a subsequent process, the beads of the first and second sets of beads may be further processed separately. The primer for each bead set may be immobilized to the beads using a variety of chemistries. Coupling may occur through, for example, amide, ester, or disulfide functional groups. Click chemistry may be used for the immobilization of the primer on beads. Immobilized primers may be further modified using additional downstream chemistry.

Prior to the method provided herein for processing a biological sample, the first set of beads and the second set of beads may be prepared (e.g., synthesized) such that a set of releasably coupled first beads and second beads is produced. After preparation, a size selection process may be performed on this set of releasably coupled first beads and second beads. The size selection step discriminates between pairs of first beads and second beads separate from other combinations of first beads and/or second beads. For example, a size selection process may discriminate between a bead pair comprising a first bead releasably coupled to a second bead and a bead pair comprising two releasably coupled first beads or a bead pair comprising two releasably coupled second beads. The first set of beads and the second set of beads may also be prepared (e.g., synthesized) such that a set of irremovably coupled first beads and second beads may be produced. Here, too, a size selection process may be performed that discriminates between different bead pairs. For example, a size selection process may discriminate between a bead pair comprising a first bead irremovably coupled to a second bead and a bead pair comprising two irremovably coupled first beads or a bead pair comprising two irremovably coupled second beads.

In the method provided herein for processing a biological sample, the one or more copies of the first strand and the one or more copies of the second strand, or complements thereof, may undergo nucleic acid sequencing. As described above, nucleic acid sequencing is a type of nucleic acid processing reaction which may include sequencing by synthesis or a polymerase chain reaction (PCR). In some methods, nucleic acid sequencing may comprise an emulsion polymerase chain reaction (emPCR).

As described above, the first strand may be coupled to a first adapter and the second strand may be coupled to a second adapter. The first and/or second adapters may participate in a nucleic acid sequencing process. The first adaptor may comprise a first sub-part and a second sub-part, which first sub-part may have sequence complementarity to the second sub-part. Sequence complementarity generally refers to sequences which are complementary to the sequence to which it is paired with. Similarly, the second adapter may comprise a first sub-part and a second sub-part, which first sub-part may have sequence complementarity to the second sub-part.

Nucleic acid sequencing may occur in a partition. This partition may comprise at least (i) one first bead from the first set of beads, (ii) at least one second bead from the second set of beads, and (iii) the biological sample comprising the first adaptor coupled to the first strand and the second adaptor coupled to the second strand. In some cases, the partition may take the form of a droplet. In some cases the partition may take the form of one or more wells.

Figure 1:
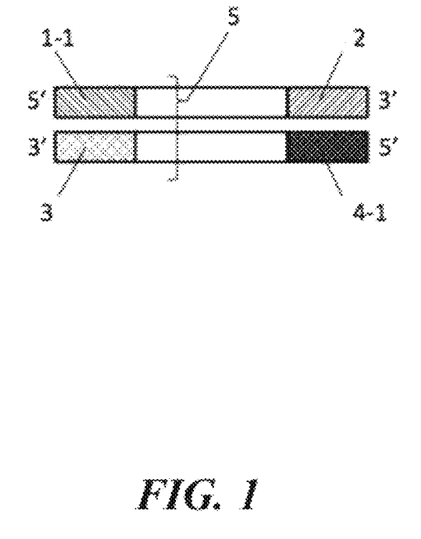
FIG. 1 depicts a schematic of the biological sample (5) flanked by distinct adaptor sequences. Adaptor A comprises Primer A (1-1) and Primer A' (3) and Adaptor B comprises Primer B (4-1) and Primer B' (2).
Figure 2:
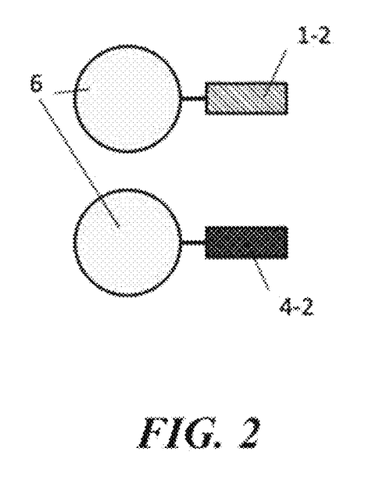
FIG. 2 depicts two types of beads. One type of bead comprises immobilized Primer A (1-2) oligonucleotides or a portion thereof. One type of bead comprises immobilized Primer B (4-2) or a portion thereof.

In a specific embodiment of the method, the method comprises providing a first bead from a first set of beads with a first primer 1-2 having sequence complementarity with a first adaptor and a second bead from a second set of beads with a second primer 4-2 having sequence complementarity with a second adaptor (see FIG. 2). The first set of beads and the second set of beads may then be randomly distributed among a plurality of partitions such that a given partition of the plurality of partitions comprises a first bead of the first set of beads and a second bead of the second set of beads. A biological sample 5 (here, a nucleic acid molecule comprising a first strand and a second strand, where the first strand has sequence complementarity to the second strand) may be selected so that nucleic acid amplification from both ends creates a region of overlap (see FIG. 1). The overlap may allow for the matching of a copy of a first strand of a biological sample, or a complement thereof, with the copy of a second strand of the biological sample, or a complement thereof. The overlap may comprise, for example, 10, 20, 30, 40, 50, 60, 70, 80, 90, 100, 110, 120, 130, 140, 150, 160, 170, 180, 190, 200, 250, 300, 350, or more base pairs (e.g., 10, 20, 30, 40, 50, 60, 70, 80, 90, 100, 110, 120, 130, 140, 150, 160, 170, 180, 190, 200, 250, 300, 350, or more nucleotides of a copy of each strand, or a complement thereof). Nucleic acid sequencing of the first and second strands, or copies or complements thereof, may provide sequence reads including all or a portion of the overlap. The region of overlap may be positioned between two adapters. For example, the first strand may comprise a first adapter and a third adapter which first and third adapters flank a first template sequence, and the second strand may comprise a second adapter and a fourth adapter which second and fourth adapters flank a second template sequence, where the first template sequence may have sequence complementarity to the second template sequence. These adapters may be single-stranded adapters. Alternatively, double-stranded adapters may be used. Such a system is depicted in FIG. 1, in which the first adapter comprises a first sub-part 1-1 and a second sub-part 3, which first sub-part may have sequence complementarity to the second sub-part. The second adaptor has a first sub-part 4-1 and a second sub-part 2, which first sub-part may have sequence complementarity to the second sub-part. The biological sample (e.g., nucleic acid molecule) comprising the first and second strand may be partitioned with a first bead from a first set of beads and a second bead from a second set of beads (e.g., as described herein), in a partition (e.g., one or more droplets or wells). The materials included in the partition may subsequently be subjected to a nucleic acid amplification reaction and/or nucleic acid sequencing. In an example, the biological sample is a nucleic acid molecule such as that depicted in FIG. 1. The nucleic acid molecule comprises a region of overlap (depicted in white) comprising a plurality of base pairs. Following partitioning in a partition with first and second beads, the materials in the partition may be subjected to nucleic acid sequencing to provide sequence reads corresponding to the first and second strands of the nucleic acid molecule. If the system read length is about 1000 nucleotides and the length of the biological sample can be about 1800 nucleotides, a sequence read of about 1000 nucleotides corresponding to the first strand and a sequence read of about 1000 nucleotides corresponding to the second strand can be generated, where the first and second sequence reads will have an overlap of about 200 nucleotides.

In a specific embodiment of the method, there is a first bead of a first set of beads with a first primer 1-2 having sequence complementarity with a first adaptor and a second bead of a second set of beads with a second primer 4-2 having sequence complementarity with a second adaptor (see FIG. 2). The first bead of the first set of beads and the second bead of the second set of beads are releasably coupled. This may form a pair of the first bead of the first set of beads and the second bead of the second set of beads. The coupling of the first bead and the second bead may be accomplished through protein interactions or covalent bonds. A set of such releasably coupled bead pairs may be prepared, in which each bead pair includes a bead of the first set of beads releasably coupled to a bead of the second set of beads. Prior to the preparation of the set of releasably coupled first beads and second beads, a size selection process is performed to discriminate between pairs of releasably coupled first beads and second beads separate from other combinations of first beads and/or second beads (e.g., a pair including two beads of the first set of beads or two beads of the second set of beads). The first bead releasably coupled to the second bead may be further subjected to stimulus (e.g., a thermal or chemical stimulus). The stimulus may release the first bead from the second bead. A biological sample 5 (e.g., a nucleic acid molecule comprising a first strand and a second strand) is selected so that nucleic acid amplification from both ends creates an overlap (see FIG. 1).

The overlap may allow for the matching of a copy of a first strand of a biological sample with the copy of a second strand of a biological sample. For example, if the system read length is about 1000 nucleotides and the length of the biological sample is about 1800 nucleotides, the overlap between a read corresponding to the first strand and a read corresponding to the second strand is about 200 nucleotides. The first and second strands of the biological sample may be flanked by two distinct adaptors, a first adaptor and a second adaptor, each of which is a double stranded adapter. The first adaptor is comprised of a first sub-part 1-1 and a second sub-part 3, which first sub-part may have sequence complementarity to the second sub-part (see FIG. 1). The second adaptor has a first sub-part 4-1 and a second sub-part 2, which first sub-part may have sequence complementarity to the second sub-part (see FIG. 1). The biological sample is then partitioned with the first bead of the first set of beads and the second bead of the second set of beads into a partition (e.g., one or more droplets or wells). The materials in the partitions are then subjected to subsequent processing such as nucleic acid amplification and nucleic acid sequencing.

In another example of the presently disclosed methods, a first bead of a first set of beads comprising a first primer 1-2 having sequence complementarity with a first adaptor and a second bead of a second set of beads comprising a second primer 4-2 having sequence complementarity with a second adaptor are provided (see FIG. 2). The first bead of the first set of beads and the second bead of the second set of beads are irreleasably coupled to form a pair including the first bead of the first set of beads and the second bead of the second set of beads. The coupling of the first bead and the second bead may be accomplished through protein interactions or covalent bonds. A set of such irreleasably coupled bead pairs may be prepared, in which each bead pair includes a bead of the first set of beads irreleasably coupled to a bead of the second set of beads. Prior to the preparation of the set of irreleasably coupled first beads and second beads, a size selection process may be performed to discriminate between pairs of first beads and second beads separate from other combinations of first beads and/or second beads (e.g., a pair including two beads of the first set of beads or two beads of the second set of beads).

A biological sample 5 (e.g., a nucleic acid molecule comprising a first strand and a second strand) is selected so that nucleic acid amplification from both ends creates an overlap (see FIG. 1). The overlap allows for the matching of a copy of a first strand of a biological sample with the copy of a second strand of a biological sample. For example, if the system read length is about 1000 nucleotides and the length of the biological sample is about 1800 nucleotides, the overlap between a read corresponding to the first strand and a read corresponding to the second strand is about 200 nucleotides. The biological sample may be flanked by two distinct adaptors, a first adaptor and a second adaptor, each of which is a double stranded adapter. The first adaptor is comprised of a first sub-part 1-1 and a second sub-part 3, which first sub-part may have sequence complementarity to the second sub-part (see FIG. 1). The second adaptor comprises a first sub-part 4-1 and a second sub-part 2, which first sub-part may have sequence complementarity to the second sub-part (see FIG. 1). The biological sample is then partitioned with the first bead of the first set of beads and the second bead of the second set of beads into a partition (e.g., one or more droplets or wells). The materials in the partitions are then subjected to subsequent processing such as nucleic acid amplification and nucleic acid sequencing.

Another aspect of the present disclosure provides a method for processing a biological sample (e.g., a nucleic acid molecule comprising a first strand and a second strand). The method may comprise providing a first set of beads and a second set of beads. A first bead of the first set of beads may comprise a first primer having sequence complementarity with a first adaptor coupled to a first strand of the biological sample. A second bead of the second set of beads may comprise a second primer having sequence complementarity with a second adaptor coupled to a second strand of the biological sample. The first primer may be different than the second primer.

The method may comprise partitioning (i) the first bead of the first set of beads, (ii) the second bead of the second set of beads, and (iii) the biological sample comprising the first adaptor coupled to the first strand and the second adaptor coupled to the second strand, in a partition. The partitioning may be achieved using, for example, droplets in an emulsion or wells.

The partition comprising the first and second beads and the biological sample may be subjected to conditions sufficient to generate one or more copies of the first strand coupled to the first adapter, or complements thereof, and/or one or more copies of the second strand coupled to the second adapter, or complements thereof. Generating the one or more copies of the first strand and/or the second strand, or complements thereof, may involve subjecting the first and second beads and the biological sample to conditions sufficient to perform a primer extension reaction and/or nucleic acid amplification reaction. The first primer of the first bead may be used to generate the one or more copies of the first strand, and/or complements thereof. The one or more copies of the first strand, and/or complements thereof, may be coupled to the first bead. The second primer of the second bead may be used to generate the one or more copies of the second strand, and/or complements thereof. The one or more copies of the second strand, and/or complements thereof, may be coupled to the second bead. The sequences of the one or more copies of the first strand, or complements thereof, may at least partially overlap the sequences of the one or more copies of the second strand, or complements thereof. As previously discussed, any type of nucleic acid amplification reaction may be used to generate an amplified product (e.g., one or more copies of the first and/or second strand, or complements thereof). The one or more copies of the first strand may have no overlap with the one or more copies of the second strand.

Another component of the partition may be a synthetic nucleic acid molecule. The synthetic nucleic acid molecule may be double stranded. The synthetic nucleic acid molecule may comprise a cleavable element. The cleavable element may allow separation of components of the synthetic nucleic acid molecule. The separation may be accomplished by chemical, light, heat or other approaches. The synthetic nucleic acid molecule may also be subjected to ligation and/or circularization. After the ligation and/or circularization occurs, the synthetic nucleic acid molecule may be cleaved to provide a cleaved synthetic nucleic acid molecule. The cleaved synthetic nucleic acid molecule may then be subjected to gap filling through an amplification reaction (e.g., as described herein).

In the presently disclosed method for processing a biological sample, the first bead of the first set of beads may be releasably coupled to the second bead of the second set of beads. For example, first bead of the first set of beads and the second bead of the second set of beads may be releasably coupled through protein interactions or covalent bonds. The protein interactions refer to hydrogen bonding or Van der Waal's forces. The covalent bonds may be formed (e.g., synthetically formed) between the beads.

The first bead releasably coupled to the second bead may be subjected to a stimulus. The stimulus causes the release of the first bead from the second bead. The stimulus may be a temperature change or a chemical stimulus. Alternatively, the first bead of the first set of beads may be irremovably coupled to the second bead of the second set of beads. This irremovable coupling may comprise cross-linking between the first bead and the second bead.

In the presently disclosed method for processing a biological sample, the method may comprise preparing (e.g., synthesizing) the first set of beads or the second set of beads. The first set of beads or the second set of beads may be, for example, polymer beads. The beads may have a coating such as a PEG layer or hydrogel. The two sets of beads may contain the same core bead or different core beads (e.g., comprise the same or different material). For example, the beads of the first set of beads may be prepared from a first material and the beads of the second set of beads may be prepared from a second material, where the first material may be the same as or different from the second material. The first and second primers may be provided to the first set of beads and the second set of beads, respectively, during the preparation (e.g., synthesis) of the first and second sets of beads. Alternatively, the first and second primers may be provided to the first set of beads and the second set of beads, respectively, after preparation of the first and second sets of beads (e.g., to "core beads" that do not yet comprise primers). Where primers are immobilized to beads in a subsequent process, the beads of the first and second sets of beads may be further processed separately. The primer for each bead set may be immobilized to the beads using a variety of chemistries. Coupling may occur through, for example, amide, ester, or disulfide functional groups. Click chemistry may be used for the immobilization of the primer on beads. Immobilized primers may be further modified using additional downstream chemistry.

In the presently disclosed method for processing a biological sample, the first set of beads and the second set of beads may be prepared such that a set of releasably coupled first beads and second beads is produced. After preparation, a size selection process may be performed on this set of releasably coupled first beads and second beads. The size selection process discriminates between pairs of first beads and second beads separate from other combinations of first beads and/or second beads. For example, a size selection process may discriminate between a bead pair comprising a first bead releasably coupled to a second bead and a bead pair comprising two releasably coupled first beads or a bead pair comprising two releasably coupled second beads. The first set of beads and the second set of beads may alternatively be prepared (e.g., synthesized) such that a set of irremovably coupled first beads and second beads is produced. Here, too, a size selection process may be performed that discriminates between different bead pairs. For example, a size selection process may discriminate between a bead pair comprising a first bead irremovably coupled to a second bead and a bead pair comprising two irremovably coupled first beads or a bead pair comprising two irremovably coupled second beads.

In the presently disclosed method for processing a biological sample, one or more copies of the first strand and one or more copies of the second strand may undergo nucleic acid sequencing. As described above, nucleic acid sequencing is a type of nucleic acid amplification reaction which may include sequencing by synthesis or a polymerase chain reaction (PCR). In some methods, nucleic acid sequencing comprises an emulsion polymerase chain reaction (emPCR).

The first adaptor may comprise a first sub-part and a second sub-part, which first sub-part has sequence complementarity to the second sub-part (e.g., as shown in FIG. 1). Sequence complementarity generally refers to a sequence which is complementary to the sequence to which it is paired with.

In some cases, each partition (e.g., droplet or well) of a plurality of partitions comprises at least one first bead of the first set of beads, at least one second bead of the second set of beads, and the biological sample comprising the first adaptor coupled to the first strand and the second adaptor coupled to the second strand. In some cases, the partition may be a droplet. In other cases, the partition may be a well.

In a specific embodiment, there are two types of beads with primer sequences matching each adaptor comprising templates identifiable by barcodes. A target nucleic acid library insert (5 in FIG. 1) length is chosen so nucleic acid sequencing from both ends provides sequence reads having no to a very minimal overlap. Inserts are end-repaired and A-tailed. A synthetic double-stranded nucleic acid molecule is designed such that it can loop and ligate with the insert. For that reason the synthetic double strand contains T overhangs preferably without terminal phosphates. The sequence of the synthetic double-stranded nucleic acid molecule is as follows: Barcode 2', PB' cleavable element, PA, Barcode 1. Barcode 1 and Barcode 2' may be known to persons skilled in the art. Barcode 1 and Barcode 2' may or may not be different sequences. However, the barcode sequences are well defined so they can be assigned to each other. The cleavable element allows separation of the strands of the synthetic double-stranded nucleic acid molecule by chemical, light, heat, or other mechanisms. After ligation and circularization, the synthetic double-stranded nucleic acid molecule will be cleaved and gap filled through polymerase-based extension. Two types of beads (6) are available for clonal amplification, one with immobilized PA (1-2) oligonucleotides or minimally a subportion of PA, and another with PB (4-2) oligonucleotides or minimally a subportion of PB immobilized. Heat denaturation of the linearized gap-filled template allows annealing to the two bead types before distribution of the beads to well-separated compartment for clonal amplification such as in emPCR. Combination of this embodiment with any of the described embodiments would allow elimination of the annealing process of a nucleic acid amplification reaction.

Computer Control Systems

Figure 6:
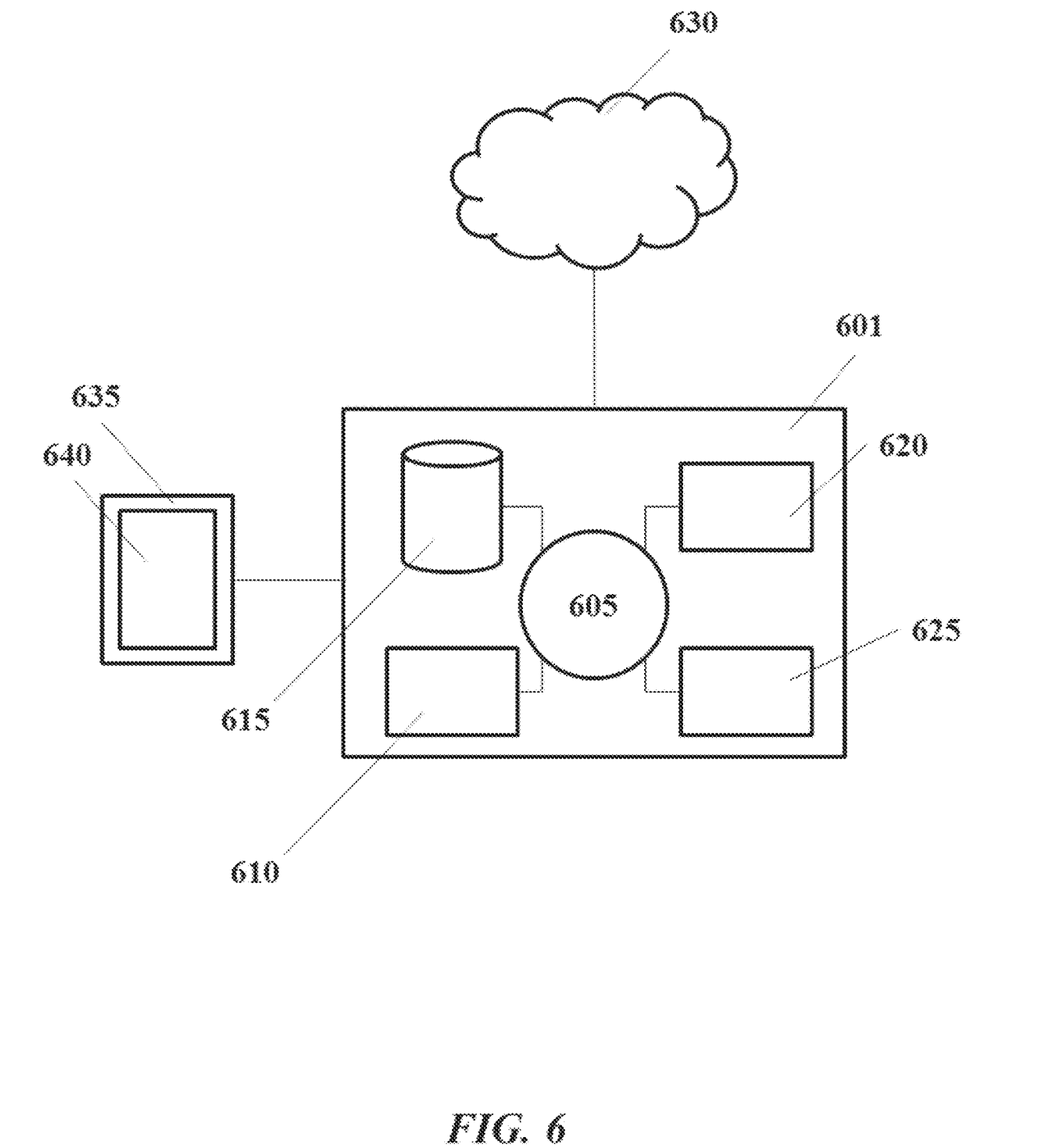
FIG. 6 shows a computer control system that is programmed or otherwise configured to implement methods provided herein.

The present disclosure provides computer control systems that are programmed to implement methods of the disclosure. FIG. 6 shows a computer system 601 that is programmed or otherwise configured to implement methods and systems of the present disclosure, such as performing nucleic acid sequence and sequence analysis.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for providing, for example, results of nucleic acid sequence (e.g., sequence reads, consensus sequences, etc.). Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, implement methods of the present disclosure.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

Example 1

FIGS. 3A, 3B, 4A, 4B, 5A, and 5B were generated from the mathematical model:

$$P_{Paired}(M_A, M_B \mid L_{droplet}, F_{split}, F_{seq}) =$$
$$\sum_{N_{droplet}} P_{Poisson}(N_{droplet} \mid L_{droplet}) \sum_{M'_A} P_{Binomial}(M'_A \mid N_{droplet}, F_{split})$$
$$P_{Binomial}(M_A \mid M'_A, F_{seq}) P_{Binomial}(M_B \mid N_{droplet} - M'_A, F_{seq})$$

where P(X|Y) indicates probability distribution of X given Y, MA and MB are the numbers of beads of population A and B, $L_{droplet}$ is the mean number of beads per droplet, $N_{droplet}$ is variable for the number of beads in droplet $F_{split}$ is the fraction of beads that are type A, $F_{seq}$ is the probability that a bead will be sequenced.

Example 2

Figure 3A:
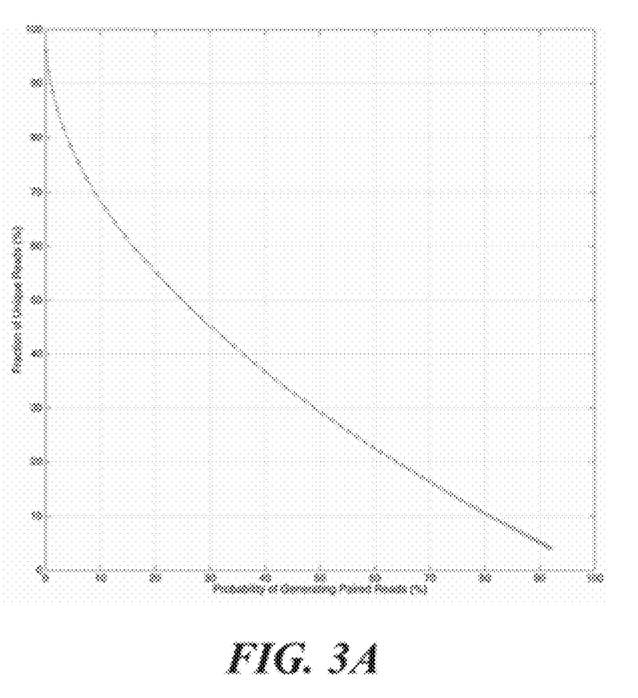
FIG. 3A and FIG. 3B shows read pairing outcomes for droplet loading, $L_{droplet}$, sweep ($F_{split}$=50%, $F_{seq}$=80%).
Figure 3B:
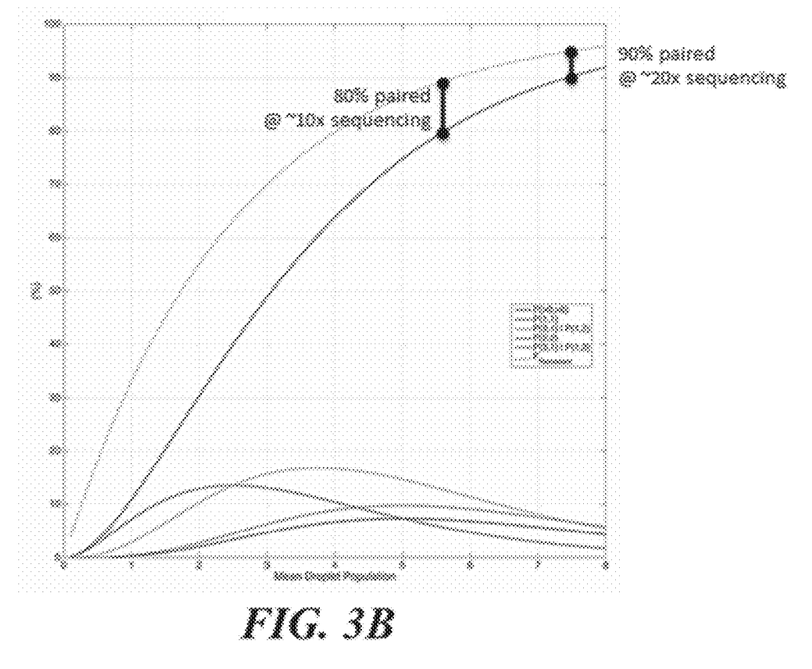

FIG. 3A shows an analytical relationship of the efficiency of random drop loading of bead types A and B. Parametrically sweeping the mean bead loading, a relationship is established between the expected fraction of unique reads and the probability of generating paired reads, i.e. at least one copy each of A and B. For example, for a 50% probability of generating paired reads, 30% of reads are unique. FIG. 3B shows the relationship between various read scenarios for a given mean droplet bead loading. The scenarios are labeled P($N_A$, $N_B$) where $N_A$ and $N_B$ are the numbers of beads of type A and B read respectively. The case $N_A$>0 and $N_B$>0, i.e. P(>0, >0), accounts for all scenarios in which an A & B read pair is obtained and is the highest solid curve. P(1,1) is the special instance in which one and only one copy of each read is obtained. The dotted curve is the fraction of reads that are redundant copies of A or B. $F_{split}$ is 50% and indicates both beads are equally likely. $F_{seq}$ is 80% and is the likelihood that a bead is sequenced. The annotation shows that attaining 80% efficiency to generate paired reads produces 90% redundancy in sequencing (additional copies of A and/or B).

Example 3

Figure 4A:
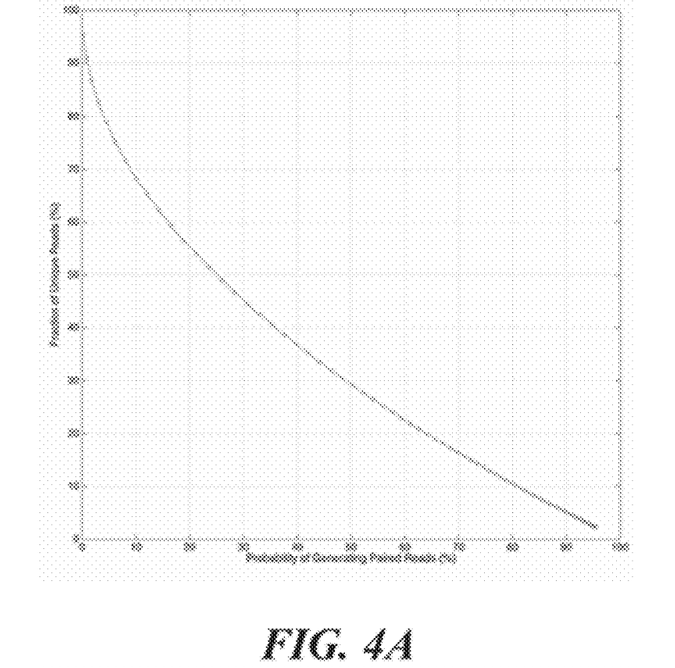
FIG. 4A and FIG. 4B shows read pairing outcomes for droplet loading, $L_{droplet}$, sweep ($F_{split}$=50%, $F_{seq}$=95%).
Figure 4B:
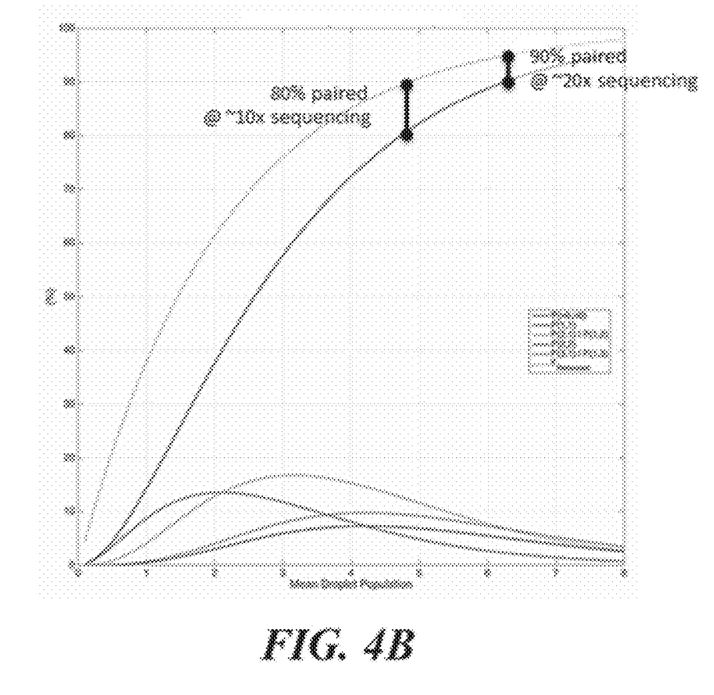

FIG. 4A shows an analytical relationship of the efficiency of random drop loading of bead types A and B. Parametrically sweeping the mean bead loading, a relationship is established between the expected fraction of unique reads and the probability of generating paired reads, i.e. at least one copy each of A and B. For example, for a 50% probability of generating paired reads, 30% of reads are unique. FIG. 4B shows the relationship between various read scenarios for a given mean droplet bead loading. The scenarios are labeled P($N_A$, $N_B$) where $N_A$ and $N_B$ are the numbers of beads of type A and B read respectively. The case $N_A$>0 and $N_B$>0, i.e. P(>0, >0), accounts for all scenarios in which an A & B read pair is obtained and is the highest solid curve. P(1,1) is the special instance in which one and only one copy of each read is obtained. The dotted curve is the fraction of reads that are redundant copies of A or B. $F_{split}$ is 50% and indicates both beads are equally likely. $F_{seq}$ is 95% and is the likelihood that a bead is sequenced. The annotation shows that attaining 95% efficiency to generate paired reads produces 90% redundancy in sequencing (additional copies of A and/or B).

Example 4

Figure 5A:
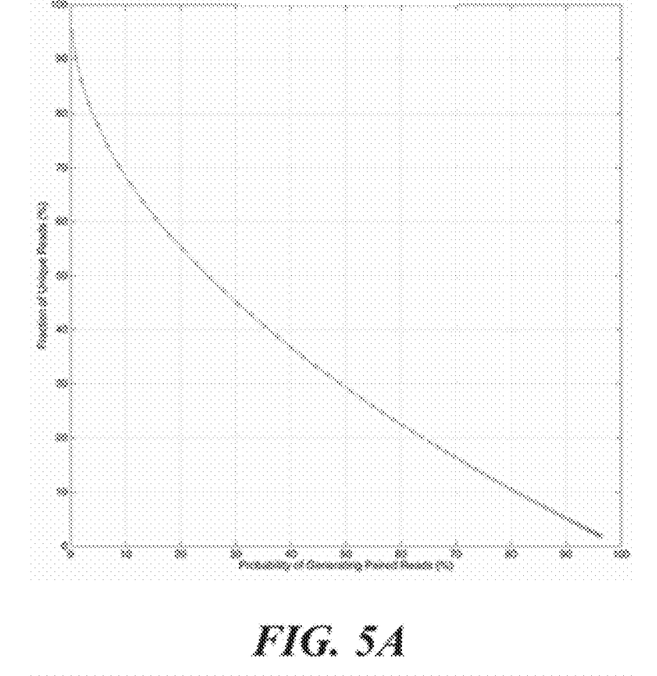
FIG. 5A and FIG. 5B shows read pairing outcomes for droplet loading, $L_{droplet}$, sweep ($F_{split}$=50%, $F_{seq}$=100%).
Figure 5B:
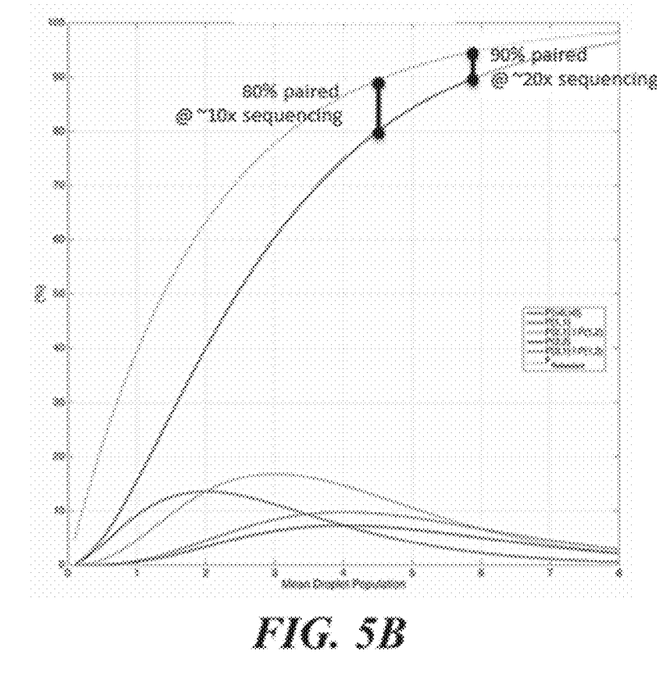

FIG. 5A shows an analytical relationship of the efficiency of random drop loading of bead types A and B. Parametrically sweeping the mean bead loading, a relationship is established between the expected fraction of unique reads and the probability of generating paired reads, i.e. at least one copy each of A and B. For example, for a 50% probability of generating paired reads, 30% of reads are unique. FIG. 5B shows the relationship between various read scenarios for a given mean droplet bead loading. The scenarios are labeled PC($N_A$, $N_B$) where $N_A$ and $N_B$ are the numbers of beads of type A and B read respectively. The case $N_A$>0 and $N_B$>0, i.e. P(>0, >0), accounts for all scenarios in which an A & B read pair is obtained and is the highest solid curve. P(1,1) is the special instance in which one and only one copy of each read is obtained. The dotted curve is the fraction of reads that are redundant copies of A or B. $F_{split}$ is 50% and indicates both beads are equally likely. $F_{seq}$ is 100% and is the likelihood that a bead is sequenced. The annotation shows that attaining 100% efficiency to generate paired reads produces 90% redundancy in sequencing (additional copies of A and/or B).

It is intended that the following claims define the scope of the invention and that methods and structures within the scope of these claims and their equivalents be covered thereby.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing a template nucleic acid comprising:
   a. providing a first set of beads and a second set of beads, wherein a first bead of the first set of beads comprises a first primer having sequence complementarity with a first adaptor coupled to a first strand of the template nucleic acid, wherein a second bead of the second set of beads comprises a second primer having sequence complementarity with a second adaptor coupled to a second strand of the template nucleic acid, wherein the first bead and the second bead are coupled;

b. coupling the template nucleic acid to the first bead and the second bead, thereby providing a bead-template complex; and c. sequencing nucleic acid molecules attached to the first bead and the second bead to generate sequencing reads corresponding to the second stand and the first strand, respectively.

2. The method of claim 1, wherein the nucleic acid molecules comprise one or more copies of the first strand and one or more copies of the second strand, and wherein a first sequence of the one or more copies of the first strand and a second sequence of the one or more copies of the second strand exhibit overlap with each other.

3. The method of claim 2, wherein the overlap comprises at least 100 nucleotides.

4. The method of claim 1, wherein the nucleic acid molecules comprise one or more copies of the first strand and one or more copies of the second strand, and wherein the one or more copies of the first strand have no overlap with the one or more copies of the second strand.

5. The method of claim 1, wherein the first bead and the second bead are coupled via a covalent bond.

6. The method of claim 1, wherein the first bead and the second bead are irreleasably coupled.

7. The method of claim 1, wherein the first bead is releasably coupled to the second bead in a releasably coupled bead pair.

8. The method of claim 7, wherein the first bead and the second bead are coupled through protein interactions or covalent bonds.

9. The method of claim 1, wherein the sequencing reads for the first strand and the second strand are matched to generate paired end reads.

10. The method of claim 9, wherein the nucleic acid molecules comprise one or more copies of the first strand and one or more copies of the second strand, and wherein the matching of the sequencing reads is based on overlap between a first sequence of the one or more copies of the first strand and a second sequence from the one or more copies of the second strand.

11. The method of claim 1, further comprising, prior to (c) subjecting the bead-template complex to conditions sufficient to amplify the first strand on the second bead and the second strand on the first bead to generate one or more copies of the first strand coupled to the second bead and one or more copies of the second strand coupled to the first bead.

12. The method of claim 11, wherein the amplification is performed in a partition.

13. The method of claim 11, wherein the amplification comprises PCR.

14. The method of claim 13, wherein the PCR comprises emulsion PCR (emPCR).

15. The method of claim 11, wherein the amplification is linear.

16. The method of claim 11, wherein the amplification is not performed in a partition.

17. The method of claim 1, wherein the first bead comprises a plurality of first primers each having sequence complementarity to the first adapter, and wherein the second bead comprises a plurality of second primers each having sequence complementarity to the second adapter.

18. The method of claim 1, wherein the sequencing comprises sequencing by synthesis.

19. The method of claim 1, further comprising, prior to (a) coupling the first bead and the second bead.

20. The method of claim 1, wherein the first primer and the second primer are different.

* * * * *